United States Patent
Banjanin et al.

(10) Patent No.: US 9,474,505 B2
(45) Date of Patent: Oct. 25, 2016

(54) PATIENT-PROBE-OPERATOR TRACKING METHOD AND APPARATUS FOR ULTRASOUND IMAGING SYSTEMS

(75) Inventors: Zoran Banjanin, Bellevue, WA (US); Christopher J. Sanders, Redmond, WA (US)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 249 days.

(21) Appl. No.: 13/422,603

(22) Filed: Mar. 16, 2012

(65) Prior Publication Data

US 2013/0245428 A1    Sep. 19, 2013

(51) Int. Cl.
*A61B 5/05* (2006.01)
*A61B 8/00* (2006.01)

(52) U.S. Cl.
CPC ........... *A61B 8/4245* (2013.01); *A61B 8/4263* (2013.01); *A61B 2034/2051* (2016.02)

(58) Field of Classification Search
CPC ................. A61B 2019/5251; A61B 8/4245; A61B 8/4263
USPC ............................. 600/407, 424, 425, 443
See application file for complete search history.

(56) References Cited

U.S. PATENT DOCUMENTS

| | | | |
|---|---|---|---|
| 5,488,952 A | 2/1996 | Schoolman | |
| 5,538,004 A | 7/1996 | Bamber | |
| 5,655,535 A | 8/1997 | Friemel et al. | |
| 5,782,766 A | 7/1998 | Weng et al. | |
| 5,899,861 A | 5/1999 | Friemel et al. | |
| 6,122,538 A * | 9/2000 | Sliwa, Jr. ................. | A61B 8/00 324/207.14 |
| 6,122,967 A * | 9/2000 | Sword ................. | G01N 29/041 73/621 |
| 6,315,724 B1 | 11/2001 | Berman et al. | |
| 6,530,885 B1 | 3/2003 | Entrekin et al. | |
| 6,785,973 B1 * | 9/2004 | Janssen ................. | G01B 5/004 33/1 N |
| 7,338,449 B2 | 3/2008 | Gueck et al. | |
| 2002/0062077 A1 * | 5/2002 | Emmenegger et al. ...... | 600/443 |
| 2005/0090742 A1 * | 4/2005 | Mine ..................... | A61B 8/0833 600/443 |
| 2006/0004290 A1 * | 1/2006 | Smith ................... | G01S 15/899 600/459 |
| 2007/0023671 A1 * | 2/2007 | Britten .................... | G01T 1/169 250/393 |
| 2007/0121113 A1 * | 5/2007 | Cohen ................... | G01N 30/74 356/432 |
| 2007/0238981 A1 * | 10/2007 | Zhu et al. ...................... | 600/424 |
| 2007/0276247 A1 | 11/2007 | Chalana et al. | |
| 2010/0041987 A1 * | 2/2010 | Manohar .............. | A61B 5/0095 600/437 |
| 2010/0249558 A1 * | 9/2010 | Yodfat .............. | A61M 5/14248 600/345 |
| 2010/0249591 A1 * | 9/2010 | Heimdal .................. | A61B 8/08 600/443 |

(Continued)

FOREIGN PATENT DOCUMENTS

| | | |
|---|---|---|
| JP | 2001-104312 A | 4/2001 |
| JP | 2006-314520 A | 11/2006 |
| JP | 2008-125692 A | 6/2008 |

*Primary Examiner* — Baisakhi Roy
(74) *Attorney, Agent, or Firm* — Kenichiro Yoshida

(57) ABSTRACT

The embodiments of the tracking device for the ultrasound imaging diagnostic apparatus include a predetermined combination of an ultrasound probe, an operator and a patient to be tracked, a space measuring device for measuring at least distance and angle of the probe based upon emitted electromagnetic radiation that is emitted towards the probe and reflected electromagnetic radiation that is reflected from the probe; and a processing device connected to the space measuring device for determining a change in distance and angle of the probe in space based upon on the emitted electromagnetic radiation and the reflected electromagnetic radiation. The space measuring device is used to track movement in a combination of a probe, a patient and an operator.

13 Claims, 8 Drawing Sheets

(56) References Cited

U.S. PATENT DOCUMENTS

| | | | |
|---|---|---|---|
| 2010/0266171 A1* | 10/2010 | Wendler | G01T 1/161 382/128 |
| 2010/0268072 A1* | 10/2010 | Hall | A61N 7/02 600/427 |
| 2012/0101388 A1* | 4/2012 | Tripathi | 600/459 |
| 2013/0150710 A1* | 6/2013 | Zentgraf | A61B 8/461 600/424 |
| 2013/0225986 A1* | 8/2013 | Eggers et al. | 600/425 |
| 2013/0237811 A1* | 9/2013 | Mihailescu et al. | 600/424 |
| 2014/0012155 A1* | 1/2014 | Flaherty | A61B 5/015 600/549 |

* cited by examiner

PATIENT-PROBE-OPERATOR TRACKING METHOD AND APPARATUS FOR ULTRASOUND IMAGING SYSTEMS

FIELD

Embodiments described herein relate generally to ultrasound diagnostic imaging systems for and method of tracking a combination of a probe position, a patient position and an operator position for ultrasound diagnostic imaging systems.

BACKGROUND

In the field of ultrasound medical examination, there have been some attempts to improve a user interface between the ultrasound imaging system and the operator. In general, an operator of an ultrasound scanner holds a probe to place it on a patient in an area of interest for scanning an image.

The probe position is tracked for certain purposes of the ultrasound imaging system. One exemplary purpose is to spatially register 2D and or 3D images with respect to the relative probe position. Spatially registered images are previously scanned or live images using the ultrasound imaging system or other modality-based medical diagnostic imaging systems such as computer tomography (CT) and magnetic resonance imaging (MRI). The fused or stitched images may be diagnostically useful in follow-ups for monitoring disease and or treatment progress.

One prior-art attempt provided a plurality of magnetic sensors for registering 2D ultrasound images with a probe position. Despite a relatively long history, the magnetic sensor has gained no wide acceptance for tracking the ultrasound sound probe since the magnetic field sensitivity is interfered due to metal objects in the room. Another reason is that the magnetic-field transducer must be altered either internally or externally to accommodate one or more sensors.

Another prior-art attempt provided an optical system of image registration. The optical system includes stereo optical cameras on a tall stand and a large target probe attachment. These additional pieces of the equipment are not practical for use with the ultrasound imaging system due to their size and costs.

In view of the above described exemplary prior-art attempts, the ultrasound imaging system still needs an improved method and device for tracking a combination of a probe position, a patient position and an operator position during the examination sessions.

DETAILED DESCRIPTION

Figure 1:
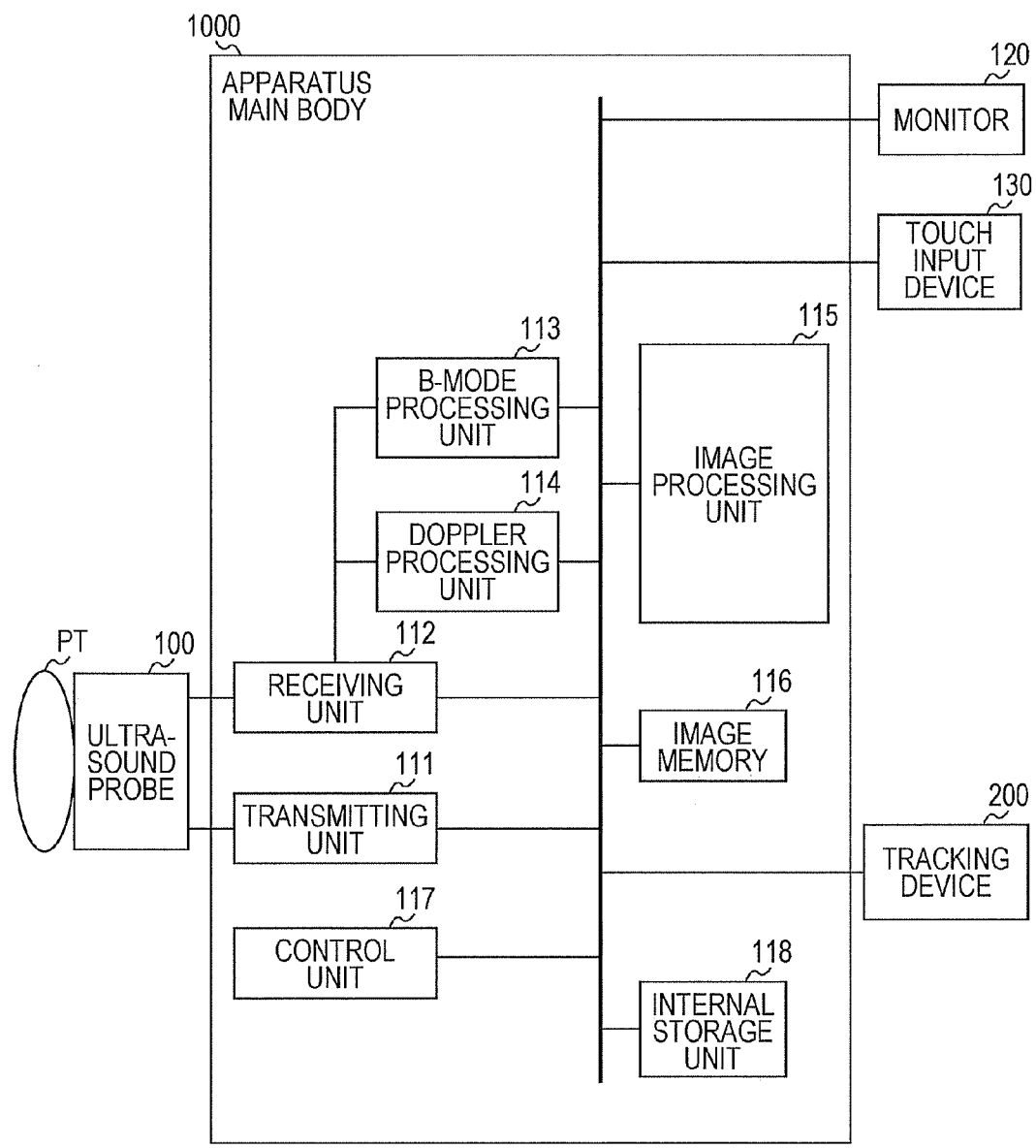
FIG. 1 is a schematic diagram illustrating an embodiment of the ultrasound diagnosis apparatus according to the current invention.

According to one embodiment, an ultrasound diagnosis apparatus includes an image creating unit, a calculating unit, a corrected-image creating unit, a probe tracking unit for tracking a probe and a display control unit. The image creating unit creates a plurality of ultrasound images in time series based on a reflected wave of ultrasound that is transmitted onto a subject from an ultrasound probe. The calculating unit calculates a motion vector of a local region between a first image and a second image that are two successive ultrasound images in time series among the ultrasound images created by the image creating unit. The corrected-image creating unit creates a corrected image from the second image based on a component of a scanning line direction of the ultrasound in the motion vector calculated by the calculating unit. The display control unit performs control so as to cause a certain display unit to display the corrected image created by the corrected-image creating unit.

Exemplary embodiments of an ultrasound diagnosis apparatus will be explained below in detail with reference to the accompanying drawings. Now referring to FIG. 1, a schematic diagram illustrates a first embodiment of the ultrasound diagnosis apparatus according to the current invention. The first embodiment includes an ultrasound probe 100, a monitor 120, a touch input device 130, a tracking device 200 and an apparatus main body 1000. One embodiment of the ultrasound probe 100 includes a plurality of piezoelectric vibrators, and the piezoelectric vibrators generate ultrasound based on a driving signal supplied from a transmitting unit 111 housed in the apparatus main body 1000. The ultrasound probe 100 also receives a reflected wave from a subject Pt and converts it into an electric signal. Moreover, the ultrasound probe 100 includes a matching layer provided to the piezoelectric vibrators and a backing material that prevents propagation of ultrasound backward from the piezoelectric vibrators.

As ultrasound is transmitted from the ultrasound probe 100 to the subject Pt, the transmitted ultrasound is consecutively reflected by discontinuity planes of acoustic impedance in internal body tissue of the subject Pt and is also received as a reflected wave signal by the piezoelectric vibrators of the ultrasound probe 100. The amplitude of the received reflected wave signal depends on a difference in the acoustic impedance of the discontinuity planes that reflect the ultrasound. For example, when a transmitted ultrasound pulse is reflected by a moving blood flow or a surface of a heart wall, a reflected wave signal is affected by a frequency deviation. That is, due to the Doppler effect, the reflected wave signal is dependent on a velocity component in the ultrasound transmitting direction of a moving object.

The apparatus main body 1000 ultimately generates signals representing an ultrasound image. The apparatus main body 1000 controls the transmission of ultrasound from the probe 100 towards a region of interest in a patient as well as the reception of a reflected wave at the ultrasound probe 100. The apparatus main body 1000 includes a transmitting unit 111, a receiving unit 112, a B-mode processing unit 113, a Doppler processing unit 114, an image processing unit 115, an image memory 116, a control unit 117 and an internal storage unit 118, all of which are connected via internal bus. The apparatus main body 1000 also optionally includes a color processing unit.

The transmitting unit 111 includes a trigger generating circuit, a delay circuit, a pulsar circuit and the like and supplies a driving signal to the ultrasound probe 100. The pulsar circuit repeatedly generates a rate pulse for forming transmission ultrasound at a certain rate frequency. The delay circuit controls a delay time in a rate pulse from the pulsar circuit for utilizing each of the piezoelectric vibrators so as to converge ultrasound from the ultrasound probe 100 into a beam and to determine transmission directivity. The trigger generating circuit applies a driving signal (driving pulse) to the ultrasound probe 100 based on the rate pulse.

The receiving unit 112 includes an amplifier circuit, an analog-to-digital (A/D) converter, an adder and the like and creates reflected wave data by performing various processing on a reflected wave signal that has been received at the ultrasound probe 100. The amplifier circuit performs gain correction by amplifying the reflected wave signal. The A/D converter converts the gain-corrected reflected wave signal from the analog format to the digital format and provides a delay time that is required for determining reception directivity. The adder creates reflected wave data by adding the digitally converted reflected wave signals from the A/D converter. Through the addition processing, the adder emphasizes a reflection component from a direction in accordance with the reception directivity of the reflected wave signal. In the above described manner, the transmitting unit 111 and the receiving unit 112 respectively control transmission directivity during ultrasound transmission and reception directivity during ultrasound reception.

The apparatus main body 1000 further includes the B-mode processing unit 113 and the Doppler processing unit 114. The B-mode processing unit 113 receives the reflected wave data from the receiving unit 112, performs logarithmic amplification and envelopes detection processing and the like so as to create B-mode data for representing a signal strength by the brightness. The Doppler processing unit 114 performs frequency analysis on velocity information from the reflected wave data that has been received from the receiving unit 112. The Doppler processing unit 114 extracts components of a blood flow, tissue and contrast media echo by Doppler effects. The Doppler processing unit 114 generates Doppler data on moving object information such as an average velocity, a distribution, power and the like with respect to multiple points.

The apparatus main body 1000 further includes additional units that are related to image processing of the ultrasound image data. The image processing unit 115 generates an ultrasound image from the B-mode data from the B-mode processing unit 113 or the Doppler data from the Doppler processing unit 114. Specifically, the image processing unit 115 respectively generates a B-mode image from the B-mode data and a Doppler image from the Doppler data. Moreover, the image processing unit 115 converts or scan-converts a scanning-line signal sequence of an ultrasound scan into a predetermined video format such as a television format. The image processing unit 115 ultimately generates an ultrasound display image such as a B-mode image or a Doppler image for a display device. The image memory 116 stores ultrasound image data generated by the image processing unit 115.

The control unit 117 controls overall processes in the ultrasound diagnosis apparatus. Specifically, the control unit 117 controls processing in the transmitting unit 111, the receiving unit 112, the B-mode processing unit 113, the Doppler processing unit 114 and the image processing unit 115 based on various setting requests that are inputted by the operator via the input devices and control programs and setting information that are read from the internal storage unit 118. For Example, the control programs executes certain programmed sequence of instructions for transmitting and receiving ultrasound, processing image data and displaying the image data. The setting information includes diagnosis information such as a patient ID and a doctor's opinion, a diagnosis protocol and other information. Moreover, the internal storage unit 118 is optionally used for storing images stored in the image memory 116. Certain data stored in the internal storage unit 118 is optionally transferred to an external peripheral device via an interface circuit. Lastly, the control unit 117 also controls the monitor 120 for displaying an ultrasound image that has been stored in the image memory 116.

A plurality of input devices exists in the first embodiment of the ultrasound diagnosis apparatus according to the current invention. Although the monitor or display unit 120 generally displays an ultrasound image as described above, a certain embodiment of the display unit 120 additionally functions as an input device such as a touch panel alone or in combination with other input devices for a system user interface for the first embodiment of the ultrasound diagnosis apparatus. The display unit 120 provides a Graphical User Interface (GUI) for an operator of the ultrasound diagnosis apparatus to input various setting requests in combination with the input device 130. The input device 130 includes a mouse, a keyboard, a button, a panel switch, a touch command screen, a foot switch, a trackball, and the like. A combination of the display unit 120 and the input device 130 optionally receives predetermined setting requests and operational commands from an operator of the ultrasound diagnosis apparatus. The combination of the display unit 120 and the input device 130 in turn generates a signal or instruction for each of the received setting requests and or commands to be sent to the apparatus main body 1000. For example, a request is made using a mouse and the monitor to set a region of interest during an upcoming scanning session. Another example is that the operator specifies via a processing execution switch a start and an end of image processing to be performed on the image by the image processing unit 115.

Still referring to FIG. 1, a plurality of input devices in the first embodiment of the ultrasound diagnosis apparatus according to the current invention additionally includes a tracking device 200. One embodiment of the tracking device 200 is connected to the apparatus main body 1000 via predetermined wired or wireless connection for sending position data or information of the probe 100 in the ultrasound diagnosis apparatus according to the current invention. For example, the probe position data includes at least a predetermined set of absolute or relative positional information of the probe 100 with respect to or within a predetermined area or space. However, the probe position data is not limited to positional data and optionally includes other information such as the angle of the probe with respect to a predetermined coordinate. Furthermore, the tracking device 200 obtains the positional information of any combination of the probe 100, a patient and an operator with respect to or within a predetermined area or space.

A first embodiment of the tracking device 200 includes other devices such as a space measuring device for measuring at least distance and angle of the probe based upon emitted electromagnetic radiation that is emitted towards the probe and reflected electromagnetic radiation that is reflected from the probe and a processing device connected to the space measuring device for determining a change in distance and angle of the probe in space based upon on the emitted electromagnetic radiation and the reflected electromagnetic radiation.

A second embodiment of the tracking device 200 includes any combination of infrared (IR) depth sensors, optical cameras, accelerometers, gyroscopes and microphones for identifying and locating any combination of a probe, an operator and a patient in a predetermined space with respect to the ultrasound diagnosis apparatus according to the current invention. For example, the microphone is utilized to identify a patient and or an operator based upon the voice analysis. The microphone may be also utilized to determine an approximate direction of a patient and or an operator with respect to the location of microphone based upon the voice analysis. Another example is that a combination of an accelerometer and a gyroscope is optionally mounted on a probe to determine an amount of change in movement, angle and or direction. Other exemplary sensors such as an IR depth sensor and an optical camera are optionally used to detect an amount of movement of a predetermined object such as a probe, an operator and a patient.

In the first or second embodiments of the ultrasound diagnosis apparatus according to the current invention, the tracking device 200 is not necessarily limited to perform the above described functions in an exclusive manner. In other embodiments of the ultrasound diagnosis apparatus according to the current invention, the tracking device 200 performs together with other devices such as the image processing unit 115 and the control unit 117 to accomplish the above described functions including the determination of the positional and angular data of the probe 100.

Figure 2A:
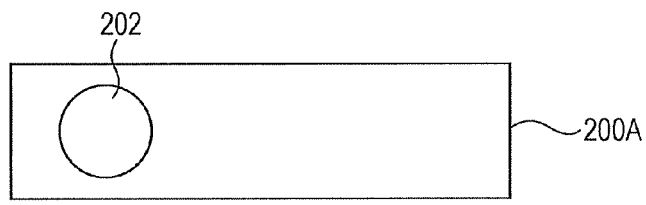
FIG. 2A is a diagram illustrating a first embodiment of the probe tracking device in the ultrasound diagnosis apparatus according to the current invention.

Now referring to FIG. 2A, a diagram illustrates one embodiment of a tracking device 200A in the ultrasound diagnosis apparatus according to the current invention. The tracking device 200A generally includes a camera or an image optical sensor 202 for capturing an image of the probe 100. The tracking device 200A optionally includes other units such as auto focus unit, a light source and so on. The above sensors in the tracking device 200A alone or in combination with other sensors detect a shape, a depth and or a movement of the probe 100 so as to generate a predetermined set of information or data such as positional data and angular data. The above sensors are merely illustrative, and the tracking device 200A according to the current invention is not limited to a particular set of sensors or sensing modes for detecting the probe 100. To facilitate the detection, the probe 100 is optionally marked or colored in predetermined manner so that the probe 100 is visibly enhanced.

Figure 2B:
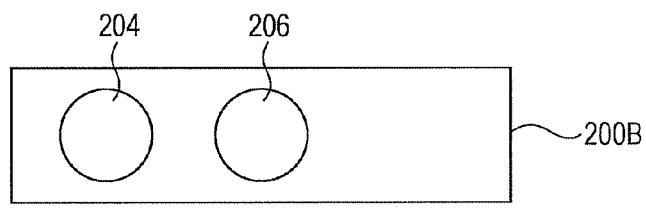
FIG. 2B is a diagram illustrating a second embodiment of the probe tracking device in the ultrasound diagnosis apparatus according to the current invention.

Now referring to FIG. 2B, a diagram illustrates another embodiment of the tracking device 200B in the ultrasound diagnosis apparatus according to the current invention. The tracking device 200B includes an infrared (IR) light source 204 and certain sensors such as an IR light sensor 206. The infrared (IR) light source 204 emits infrared towards the probe 100 while the IR light sensor 206 receives the infrared reflected from the probe 100. Although the illustrated embodiment of the tracking device 200B has a separate position for the IR light source 204 and the IR light sensor 206, the position may be identical. Furthermore, the infrared range is not also limited and is optionally outside of the IR range of the electromagnetic radiation. The above sensors in the tracking device 200B alone or in combination with other sensors detect a shape, a depth and or a movement of the probe 100 so as to generate a predetermined set of information or data such as positional data and angular data. The above sensors are merely illustrative, and the tracking device 200B according to the current invention is not limited to a particular set of sensors or sensing modes for detecting the probe 100.

Figure 2C:
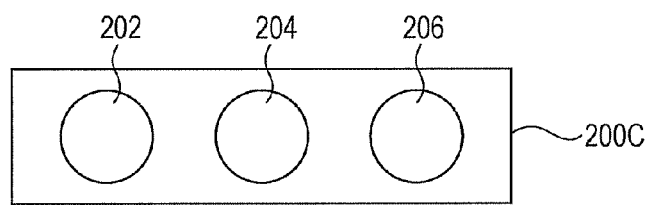
FIG. 2C is a diagram illustrating a third embodiment of the probe tracking device in the ultrasound diagnosis apparatus according to the current invention.

Now referring to FIG. 2C, a diagram illustrates yet another embodiment of the tracking device 200C in the ultrasound diagnosis apparatus according to the current invention. The tracking device 200C includes a camera or an image optical sensor 202 for capturing an image of the probe 100. The tracking device 200C also includes an infrared (IR) light source 204 and certain sensors such as an IR light sensor 206. The infrared (IR) light source 204 emits infrared towards the probe 100 while the IR light sensor 206 receives the infrared reflected from the probe 100. Although the illustrated embodiment of the tracking device 200C has a separate position for the IR light source 204 and the IR light sensor 206, the position may be identical. Furthermore, the infrared range is not also limited and is optionally outside of the IR range of the electromagnetic radiation. The above multiple sensors in the tracking device 200C alone or in combination with other sensors detect a shape, a depth and or a movement of the probe 100 so as to generate a predetermined set of information or data such as positional data and angular data. In the above exemplary embodiment, the tracking device 200C emits and receives invisible electromagnetic radiation while it also captures an image using the visible light range. The above sensors are merely illustrative, and the tracking device 200C according to the current invention is not limited to a particular set of sensors or sensing modes for detecting the probe 100.

The above described embodiments are merely illustrative of the inventive concept of tracking a probe in the ultrasound diagnostic imaging system according to the current invention. In general, the larger a number of the above described sensors the probe tracking device has, the more accurate the predetermined information the probe tracking device generates, assuming that the resolution of the sensors is not yet met by a plurality of the sensors. Furthermore, the accuracy of the information depends upon the resolution of the sensors.

Figure 3A:
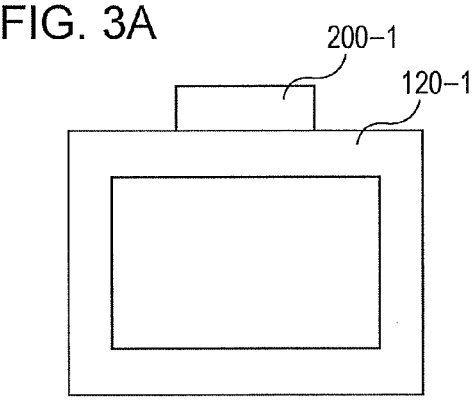
FIG. 3A is a diagram illustrating a first embodiment of the probe tracking device, which is mounted on a top of a display unit.
Figure 3B:
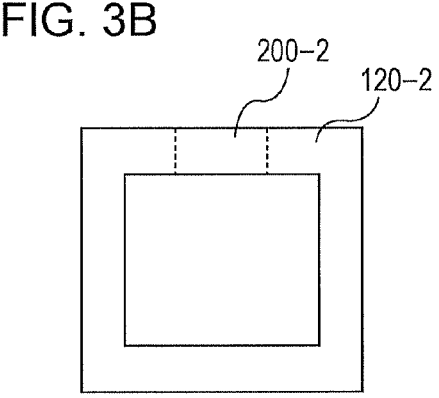
FIG. 3B is a diagram illustrating a second embodiment of the probe tracking device, which is integrated in a top of a display unit.

Now referring to FIGS. 3A and 3B, the tracking device 200 is implemented in various manners in the ultrasound diagnosis apparatus according to the current invention. FIG. 3A illustrates a first embodiment of a tracking device 200-1, which is mounted on a top of a display unit 120-1. The mounting is not limited on the top of the display unit 120-1 and includes any other surfaces of the display unit 120-1 or even other units or devices in or outside the ultrasound diagnosis apparatus according to the current invention. Depending upon implementation, the tracking device 200-1 is optionally mounted on the display unit 120-1 in a retrofitted manner in an existing ultrasound diagnosis apparatus system. One embodiment of the tracking device 200-1 includes an IR light and a depth image detector according to the current invention.

FIG. 3B illustrates a second embodiment of a tracking device 200-2, which is integrated in a top portion of a display unit 120-2 as indicated by the dotted lines. The integration is not limited to the top portion of the display unit 120-2 and includes any other portions of the display unit 120-2 or even other units or devices in the ultrasound diagnosis apparatus according to the current invention. One embodiment of the tracking device 200-2 includes an IR light and a depth image detector according to the current invention.

As already described with respect to FIGS. 2A, 2B and 2C, one embodiment of the probe tracking device is a separate unit and is placed next to a predetermined location near an existing device such as a display unit. The placement is not limited to the side of the display unit and includes any other locations or even other units or devices in or outside the ultrasound diagnosis apparatus according to the current invention. Depending upon implementation, the probe tracking device is optionally placed near the display unit or other devices to be incorporated into in an existing ultrasound diagnosis apparatus system in a retrofitted manner.

Figure 4:
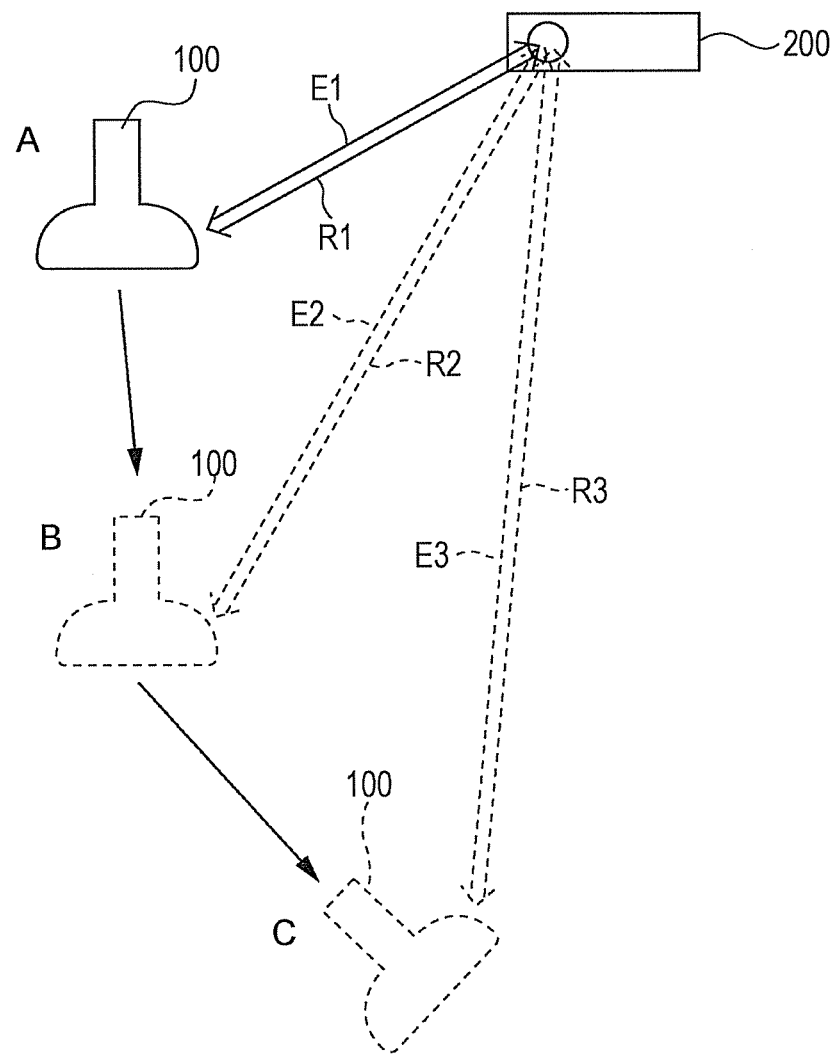
FIG. 4 is a diagram illustrating an exemplary operation of one embodiment of the probe tracking device in the ultrasound imaging and diagnosis system according to the current invention.

Now referring to FIG. 4, a diagram illustrates an exemplary operation of one embodiment of the probe tracking device in the ultrasound imaging and diagnosis system according to the current invention. For example, while an operator OP holds the probe 100 for scanning an ultrasound image, the tracking device 200 emits a predetermined range of electromagnetic radiation or light towards the probe 100 as indicated as E1 at a position A. Although only a single ray E1 is illustrated, the tracking device 200 generally emits a group of rays in certain broad directions from a predetermined stationary position. The predetermined rage of the electromagnetic radiation includes both visible and invisible range and is not limited to a particular narrow range. As the electromagnetic radiation that has been emitted from the tracking device 200 reaches the probe 100, the emitted electromagnetic radiation is reflected on a surface of the probe 100.

The probe 100 reflects the emitted light back towards the tracking device 200 as indicated as R1 from the position A. The tracking device 200 receives the reflected electromagnetic radiation. The tracking device 200 determines a change in distance and angle of the probe 100 in a predetermined space based upon on the emitted electromagnetic radiation and the reflected electromagnetic radiation. Lastly, the tracking device 200 outputs the change in an ultrasound imaging system. In one example, a display unit displays the change. In another example, the ultrasound imaging system uses the change in the probe position for a particular application such as stitching the previously stored images as will be further described.

In this example, it is assumed that the probe 100 is not stationary as indicated by the arrows and dotted lines. That is, the probe 100 moves from the position A to a position C via a position B. As the probe 100 moves from one position to another, the tracking device 200 continuously monitors the position and the angle of the probe 100 by repeatedly emitting the predetermined range of electromagnetic radiation towards the probe 100 and receiving the reflected electromagnetic radiation from the probe 100. At the position B, the tracking device 200 respectively emits and receives the electromagnetic radiation rays E2 and R2 as indicated in dotted lines to and from the probe 100. By the same token, at the position C, the tracking device 200 respectively emits and receives the electromagnetic radiation rays E3 and R3 as indicated in dotted lines to and from the probe 100. As the tracking device 200 monitors the moving probe 100, the tracking device 200 determines a change in distance and angle of the probe 100 in a predetermined space based upon on the emitted electromagnetic radiation rays E1, E2, E3 and the reflected electromagnetic radiation rays R1, R2, R3.

In order to have an efficient and accurate monitoring operation, the electromagnetic radiation is reflected from the probe. Although the reflecting surface of the probe 100 is not limited to any particular surface, one embodiment of the probe 100 is optionally manufactured to have a predetermined coat that is suitable for reflecting a particular frequency range of light. In another embodiment, the probe 100 is optionally manufactured to have a predetermined reflector element in lieu of the coating surface.

Figure 5:
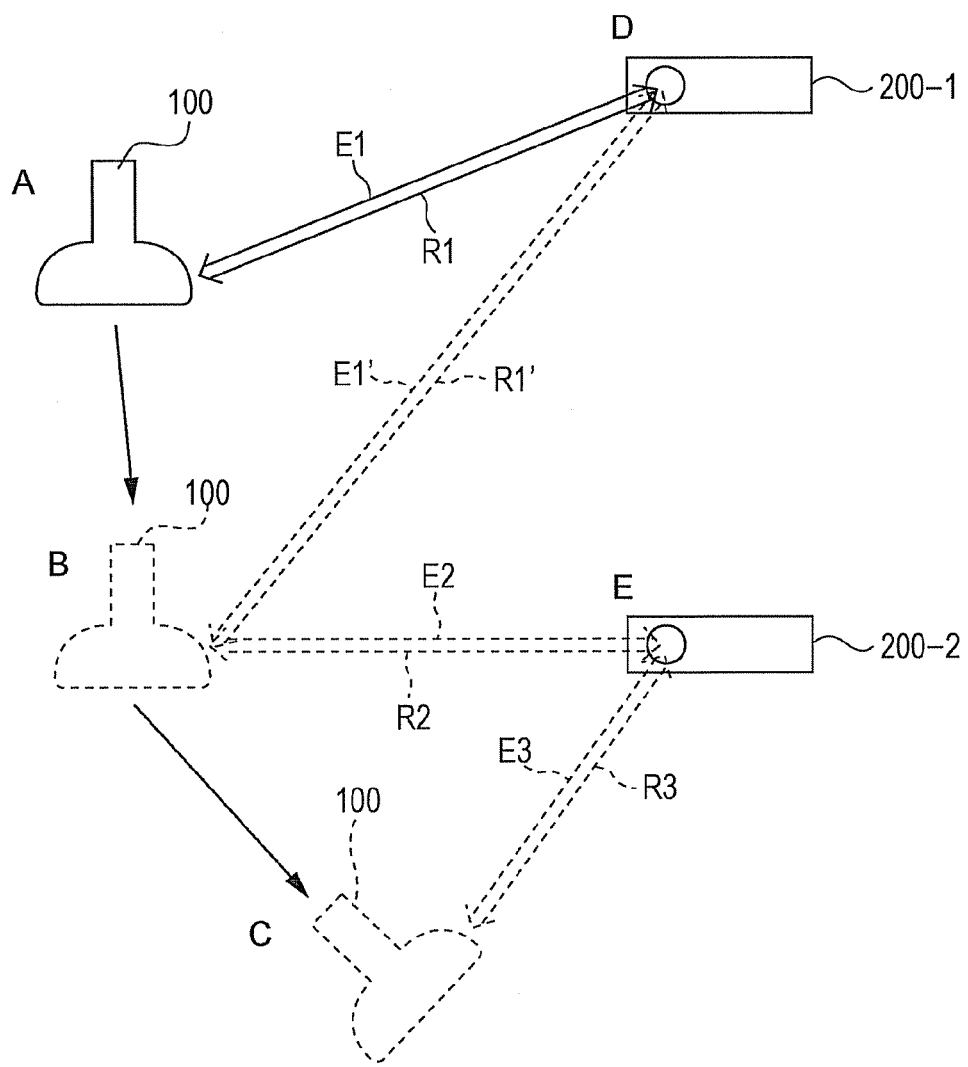
FIG. 5 is a diagram illustrating an exemplary operation of another embodiment of the probe tracking device in the ultrasound imaging and diagnosis system according to the current invention.

Now referring to FIG. 5, a diagram illustrates an exemplary operation of one embodiment of the probe tracking device in the ultrasound imaging and diagnosis system according to the current invention. For example, while an operator OP holds a probe 100 for scanning an ultrasound image, a tracking device 200-1 emits a predetermined range of electromagnetic radiation or light towards the probe 100 as indicated as E1 at a position A. Although only a single ray E1 is illustrated, the tracking device 200-1 generally emits a plurality of rays in certain broad directions. The predetermined rage of the electromagnetic radiation includes both visible and invisible range and is not limited to a particular range.

In the above exemplary embodiment, it is assumed that the probe 100 is not stationary as indicated by the arrows and dotted lines. That is, the probe 100 moves from the position A to a position C via a position B. As the probe 100 moves from one position to another, the tracking device 200-1 continuously monitors the position and the angle of the probe 100 by repeatedly emitting the predetermined range of electromagnetic radiation towards the probe 100 and receiving the reflected electromagnetic radiation from the probe 100. At the same time, a second tracking device 200-2 also continuously monitors the position and the angle of the probe 100 by repeatedly emitting the predetermined range of electromagnetic radiation towards the probe 100 and receiving the reflected electromagnetic radiation from the probe 100. The tracking device 200-1 is located at a position D while the tracking device 200-2 is located at a position E through out the course of monitoring the probe 100.

In the above exemplary embodiment of the ultrasound imaging and diagnosis system according to the current invention, a plurality of the probe tracking devices simultaneously monitors the positional and or angular change of the probe 100 in a predetermined space. That is, when the probe 100 is at the position A, the tracking device 200-1 at the position D alone emits and receives respective electromagnetic radiation rays E1 and R1 as indicated in dotted lines to and from the probe 100. When the probe 100 is at the position B, the probe tracking devices 200-1 and 200-2 both emit respective electromagnetic radiation rays E1' and E2. When the probe 100 is also at the position B, the probe tracking devices 200-1 and 200-2 respectively receive the electromagnetic radiation rays R1' and R2. On the other hand, when the probe 100 is at the position C, the tracking device 200-2 at the position E alone emits and receives respective electromagnetic radiation rays E3 and R3 as indicated in dotted lines to and from the probe 100.

Still referring to FIG. 5, as the probe tracking devices 200-1 and 200-2 monitor the moving probe 100, the probe tracking devices 200-1 and 200-2 in combination determine a change in distance and angle of the probe 100 in a predetermined space based upon on the emitted electromagnetic radiation rays E1, E1', E2, E3 and the reflected electromagnetic radiation rays R1, R1', R2, R3. In the above exemplary embodiment, it is assumed that the probe tracking devices 200-1 and 200-2 are located respectively at the positions D and E in a fixed manner. In another embodiment, any combination of the probe 100 and the probe tracking devices 200-1 and 200-2 is optionally moving during the course of monitoring the position and or the angle of the probe 100 in a predetermined space. Furthermore, the movement of the probe 100, the tracking device 200-1 or the tracking device 200-2 is not necessarily coordinated or synchronous.

In alternative embodiment, a single probe tracking device houses a plurality of spatially separated sensors to monitor the moving probe 100 and to determine a change in distance and angle of the probe 100 in a predetermined space based upon on the electromagnetic radiation rays.

With respect to FIGS. 4 and 5, the use of electromagnetic radiation is not limited to a particular range and includes at least infrared radiation and or visible radiation. Although the diagrams in FIGS. 4 and 5 do not explicitly illustrate, the use of electromagnetic radiation requires a plurality of hardware and software for sensing movement and angle according to the current invention. When visible light is used, one embodiment of the tracking device 200 includes a predetermined sensor such as a stereoscopic optical sensor to estimate depth dimension based upon images that have been captured by at least two spatially separated cameras. In case of visible light, electromagnetic radiation is not necessarily emitted from a particular source if a sufficient amount of visible light is available in the environment.

Still referring to FIGS. 4 and 5, in other embodiments of the tracking device 200, additional techniques are used. In one embodiment, infrared is used with a predetermined light coding technique to estimate depth dimension. The observed volume is coded by infrared, and a predetermined single CMOS depth image sensor detects the coded light from the observed volume. Furthermore, a "time-of-flight" technique is optionally used in another embodiment to acquire depth based upon a 3D camera or a time-of-flight camera for measuring the time-of-flight of a light signal between the camera and the subject for each point of the image. The time-of-flight camera is a class of scannerless Light Detection And Ranging (LIDAR) in which the entire image is captured with each laser or light pulse as opposed to point-by-point with a laser beam such as in scanning LIDAR systems. The light pulse includes ultraviolet, visible, or near infrared light. In order to practice the probe tracking, any combination of the above described techniques is implemented to determine the depth, movement and or angle of the probe within or with respect to a predetermined space in relation to the ultrasound imaging and diagnosis system according to the current invention.

FIGS. 4 and 5 illustrate that the tracking device 200 monitors and determine the movement of the probe 100 as an example. The tracking device 200 is not limited to track the movement of the probe 100 and is optionally used to monitor a plurality of predetermined objects in a simultaneous manner. In one embodiment, the tracking device 200 monitors the movement of any combination of the probe 100, a patient on which the probe is placed and an operator who places the probe 100 on the patient using a predetermined set of the sensors as described above. In this regard, one embodiment of the tracking device 200 provides multiple sets of relative or absolute positional and angular data for the predetermined objects in a continuous manner.

Figure 6:
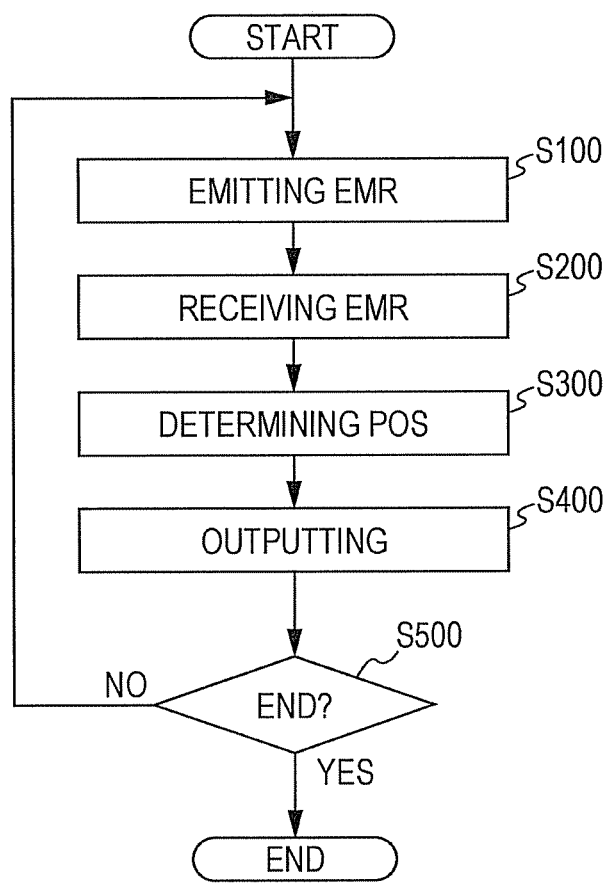
FIG. 6 is a flow chart illustrating steps involved in one process of tracking a probe in the ultrasound imaging and diagnosis system according to the current invention.

Now referring to FIG. 6, a flow chart illustrates steps involved in one process of tracking a probe in the ultrasound imaging and diagnosis system according to the current invention. The flow chart is exemplary and general and is not limited to a particular probe tracking process of the current invention. For these reasons, the electro magnetic radiation (EMR) is utilized to include at least visible light range and an infrared range of the electromagnetic spectrum. On the other hand, the probe tracking process according to the current invention is not limited to using a particular range of the electromagnetic spectrum and or a particular combination of the sensors. In a step S100, a predetermined range or ranges of EMR is emitted from a predetermined position towards a probe to be tracked. If a visible range is utilized, it is not necessarily emitted from a particular source unless there is not a sufficient amount of visible light is available in a predetermined space where the probe is tracked. In this regard, the step S100 of emitting is optionally tantamount to providing EMR if visible light is available from the environment.

In a step S200, the EMR that has been substantially reflected from the probe is received in one embodiment of the current process. In another embodiment, while the EMR may be partially absorbed by the probe, EMR is still partially reflected from the probe and also received in the step S200. Thus, the predetermined range or range or ranges of EMR are received by a predetermined detector or sensor from the probe to be tracked. If a visible range is utilized, an image is captured by an optical camera. On the other hand, if a predetermined laser beam is used, a LIDAR camera captures the laser data. In any case, some reflected EMR is received in the step S200 at a predetermined position with respect to the emitting position of the step S100. In one embodiment of the current process, the received position and the emitting position are substantially identical. In another embodiment of the current process, the received position and the emitting position are substantially different. In this regard, there may be a substantial delay in emitting and receiving between the steps S100 and S200.

The steps S100 and S200 are performed in a variety of manners according to the current invention. For example, the emitting and receiving steps S100 and S200 are automatically activated and continuously performed only when the probe is in motion in one embodiment of the current process. In another embodiment of the current process, the steps S100 and S200 are not performed while the probe is stationary. In yet another embodiment of the current process, the steps S100 and S200 are manually activated to perform.

In a step S300, spatial information of the probe is determined according to the emitted EMR in the step S100, the received EMR in the step S200. In one embodiment of the current process, the emitted EMR in the step S100 is visible, and the received EMR in the step S200 is an image of the probe. The step S300 determines the spatial information of the probe based upon the images in the above visible EMR embodiment. On the other hand, in another embodiment of the current process, the emitted EMR in the step S100 is infrared, and the received EMR in the step S200 is infrared EMR data of the probe. The step S300 determines the spatial information of the probe based upon the infrared EMR data in the above infrared EMR embodiment. In yet another embodiment of the current invention, both the visible range and the infrared range of EMR are utilized, and the step S300 determines the spatial information of the probe based upon a combination of the images and the infrared EMR data. In any case, the spatial information includes any combination of absolute coordinates, relative movement in distance, speed, acceleration and angular change of the probe within the predetermined space.

After determining the spatial information in the step S300, the spatial information is outputted in a step S400 of the current process of tracking the probe in the ultrasound imaging and diagnosis system according to the current invention. In one embodiment of the current process, the outputting step S400 involves displaying of the data. For example, the displayed data is one of a 2D image, a 3D image and a 4D image that are based upon previously stored data and that corresponds to the change in spatial information with respect to the probe. Another exemplary displayed data is a 3D volume that is stitched together from a plurality of previously stored 3D volumes. Yet another exemplary displayed data is a 3D volume that is stitched together from a plurality of previously stored 2D images. An additional exemplary displayed image is an image that is based upon imaging data that is acquired by the probe that has been monitored for tracking according to a process of the current invention.

Still referring to FIG. 6, the above described steps S100 through S400 are repeated until a predetermined condition is achieved in a step S500 in one embodiment of the current process. For example, the steps S100 through S400 are automatically activated and continuously performed while the probe is determined to be in motion in the step S500 in one embodiment of the current process. In another embodiment of the current process, the steps S100 through S400 are manually deactivated in the step S500.

Figure 7:
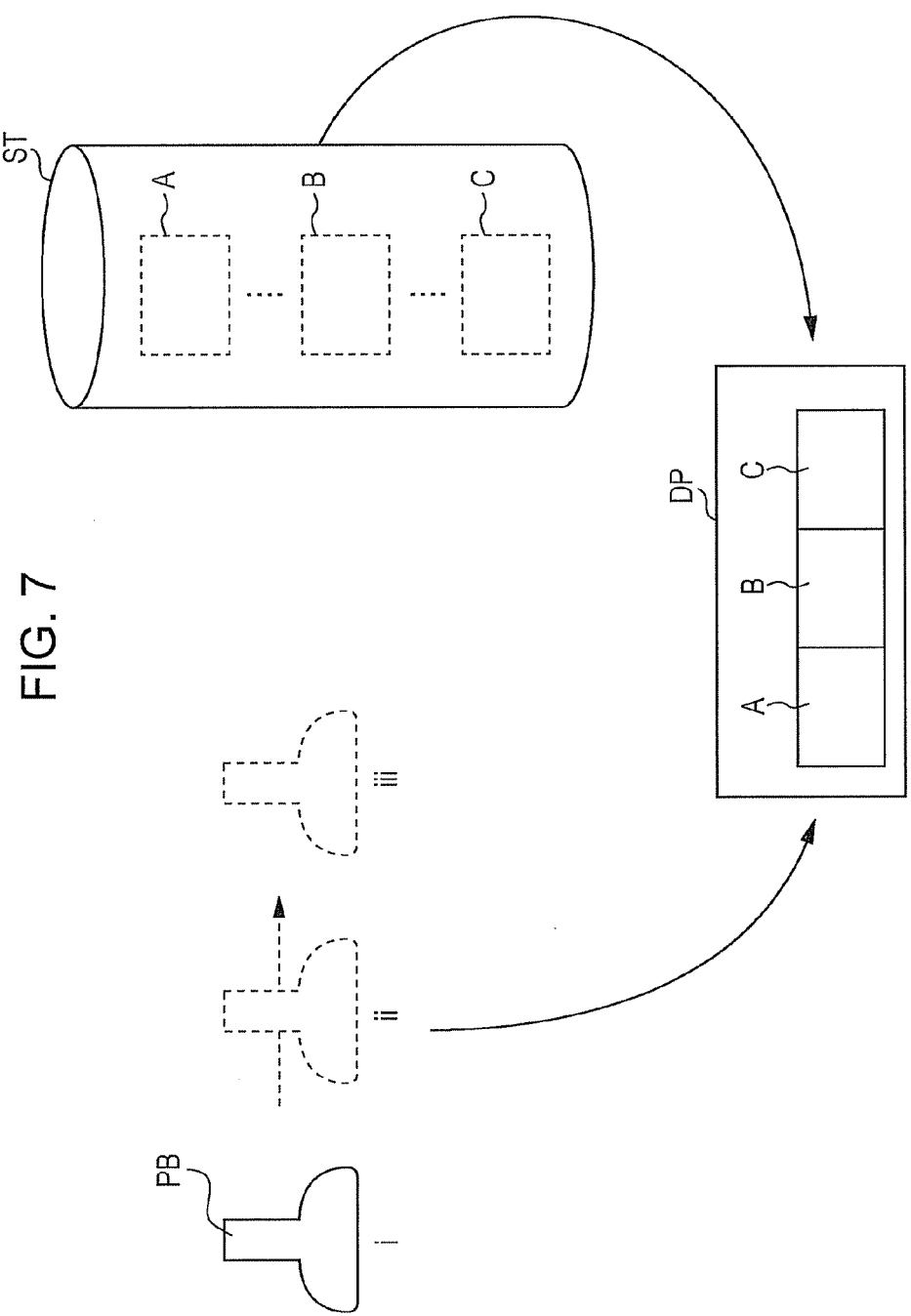
FIG. 7 is a diagram illustrating steps involved in one process of tracking a probe position and utilizing the position information in the ultrasound imaging and diagnosis system according to the current invention.

Now referring to FIG. 7, a diagram illustrates steps involved in one process of tracking a probe position and utilizing the position information in the ultrasound imaging and diagnosis system according to the current invention. In an exemplary process, a probe PB is moved from a first position i to a third position iii through a second position ii over a patient's body surface in order to scan a region of interest for ultrasound imaging. As the probe PB travels, the above described process as illustrated in the flow chart of FIG. 6 determines an amount of the probe movement in direction and or angle based upon the electromagnetic radiation as detected with respect to the probe PB.

Based upon the probe tracking information as determined by the above described process as illustrated in the flow chart of FIG. 6, a set of previously stored images are selected from a storage device ST. The previously stored images includes the region of interest that has been currently scanned by the probe PB and are generally acquired by an imaging and diagnosis system of modalities such as Xray-based computer tomography (CT) and magnetic resonance imaging (MRI), which generally provides a higher resolution than the ultrasound imaging. A corresponding set of the high-resolution images is selected from the storage device ST for displaying based upon the probe tracking information as indicated by the arrows. For example, as the probe PB travels from the first position ii to the third position iii through the second position ii, the corresponding images A, B and C are optionally displayed on a monitor DP in a predetermined manner. The images A, B and C are sequentially displayed in a real time in one implementation mode while they may be stitched together in another implementation mode. The previously stored images are not limited to a different modality and also optionally includes ultrasound images.

Still referring to FIG. 7, the displayed data additionally include other images that are generated from a variety of previously stored images data. For example, the displayed image is one of a 2D image, a 3D image and a 4D image that are based upon previously stored data and that corresponds to the change in spatial information with respect to the probe. Another exemplary displayed image is a 3D volume that is stitched together from a plurality of previously stored 3D volumes. Yet another exemplary displayed data is a 3D volume that is stitched together from a plurality of previously stored 2D images. An additional exemplary displayed image is an image that is based upon imaging data that is acquired by the probe that has been monitored for tracking according to a process of the current invention.

Figure 8:
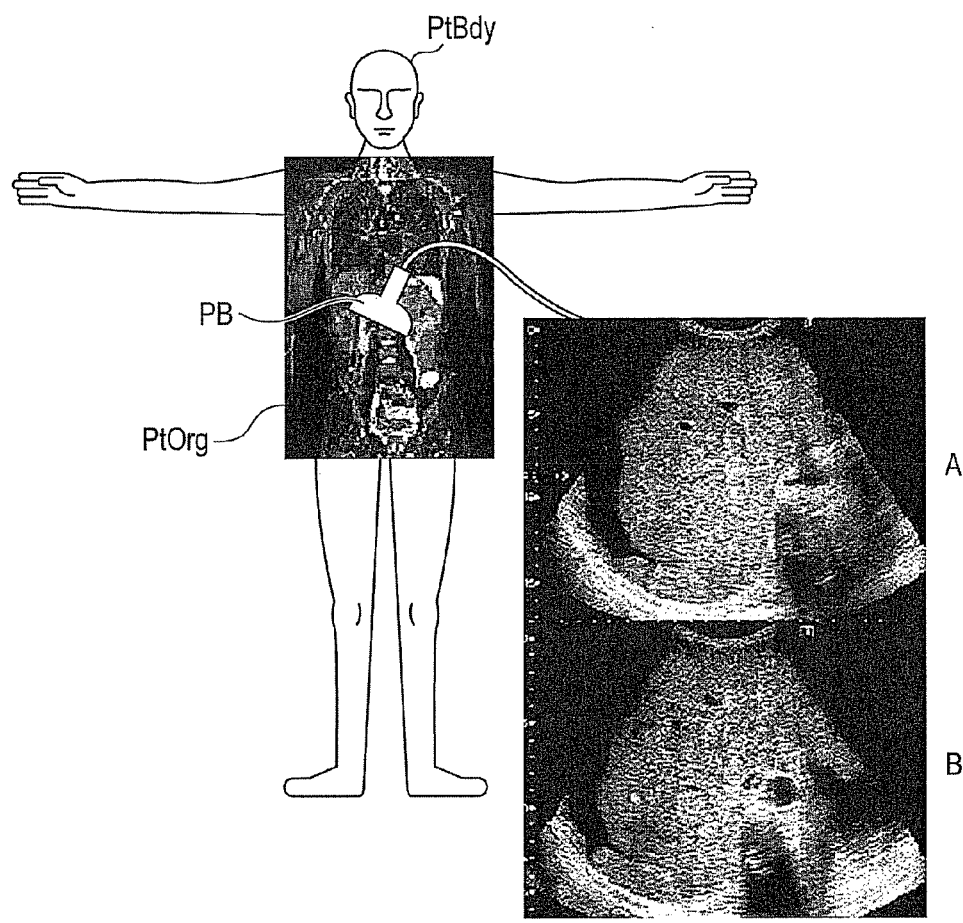
FIG. 8 is a diagram illustrating an exemplary display of tracking a combination of a probe and a patient in the ultrasound imaging system according to the current invention.

Now referring to FIG. 8, a diagram illustrates an exemplary display of tracking a combination of a probe and a patient in the ultrasound imaging system according to the current invention. In this exemplary display, a patient is lying down on his back, and the legs and arms are extended as shown in a patient image PtBdy. The patient image PtBdy is captured by a predetermined camera or 3D capturing device and stored. By the same token, a patient organ image PtOrg is previously captured by a conventional X-ray, magnetic resonance imaging (MRI) or computed tomography (CT) scanner. In one exemplary display, the patient organ image PtOrg is superimposed on the patient image PtBdy. Although the body image and the internal organ image are both extensive in the exemplary display, either or both of the images are optionally localized to a smaller portion of the body or the organ(s) for display. In a certain implementation, the above images are optionally zoomed.

In an exemplary process, a probe PB is moved to a current probe position i on a patient's body surface in order to scan a region of interest for ultrasound imaging. The current position i of the probe PB is determined with respect to the patient body PtBdy, and an ultrasound image A is displayed at the current probe position i. As the current position i changes, the ultrasound image A also changes unless the operator optionally freezes the image A. After the operator determines a desirable ultrasound image for a particular organ of interest, the relevant positional information is stored along with the scanned ultrasound image at the established position I for the future use. Subsequently, the ultrasound image is scanned at the exact previously established probe position I for various purposes. For example, the chronologically scanned images are compared to determine the effect of a cancer treatment on the organ at the exactly identical location. Assuming that an ultrasound image B is previously scanned image before a predetermined treatment, the comparison of the images A and B are effective in determining the effect of the treatment.

Still referring to FIG. 8, to have an effective comparison in the above example, the ultrasound images A and B have to be scanned at the exactly identical location of the same organ. To facilitate the above identification task, as the operator moves the probe PB over the patient body PtBdy to identify the previously established probe position I with a visual aid in the ultrasound imaging system according to the current invention. For example, a predetermined icon indicates the current probe position i on the image of the patient body PtBdy to provide a visual feedback to the operator who is trying to identify the previously established position I, which is also indicated by another predetermined icon. As the probe PB moves, the above described process as illustrated in the flow chart of FIG. 6 determines an amount of the probe movement in direction and or angle based upon the electromagnetic radiation as reflected from the probe PB. Based upon the detected probe movement, the display icon of the current probe position i is also determined with respect to the patient body image PtBdy. Upon matching the position icons, additional visual feedback is optionally provided for matching the angle of the probe PB and the previously established angle among other things.

Without the above described visual aid, the operator relies only upon the anatomical landmarks of the scanned ultrasound image to identify the previously established position I. On the other hand, over the course of certain treatment, the landmarks may become unclear due to the visual changes in the region of interest. According to the exemplary process of the current invention, the previously established position I is ascertained based upon the above described visual aid that is based upon the probe PB position with respect to the patient PtBdy even without relying upon anatomical knowledge.

Based upon the probe tracking information as determined by the above described process, a set of previously stored images are selected from a storage device ST. The previously stored images includes the region of interest that has been currently scanned by the probe PB and are generally acquired by an imaging and diagnosis system of modalities such as Xray-based computer tomography (CT) and magnetic resonance imaging (MRI), which generally provides a higher resolution than the ultrasound imaging. A corresponding set of the high-resolution images is selected from the storage device ST for displaying based upon the probe tracking information. Furthermore, the displayed data additionally include other images that are generated from a variety of previously stored images data. For example, the displayed image is one of a 2D image, a 3D image and a 4D image that are based upon previously stored data and that corresponds to the change in spatial information with respect to the probe. Another exemplary displayed image is a 3D volume that is stitched together from a plurality of previously stored 3D volumes. Yet another exemplary displayed data is a 3D volume that is stitched together from a plurality of previously stored 2D images. An additional exemplary displayed image is an image that is based upon imaging data that is acquired by the probe that has been monitored for tracking according to a process of the current invention.

Figure 9:
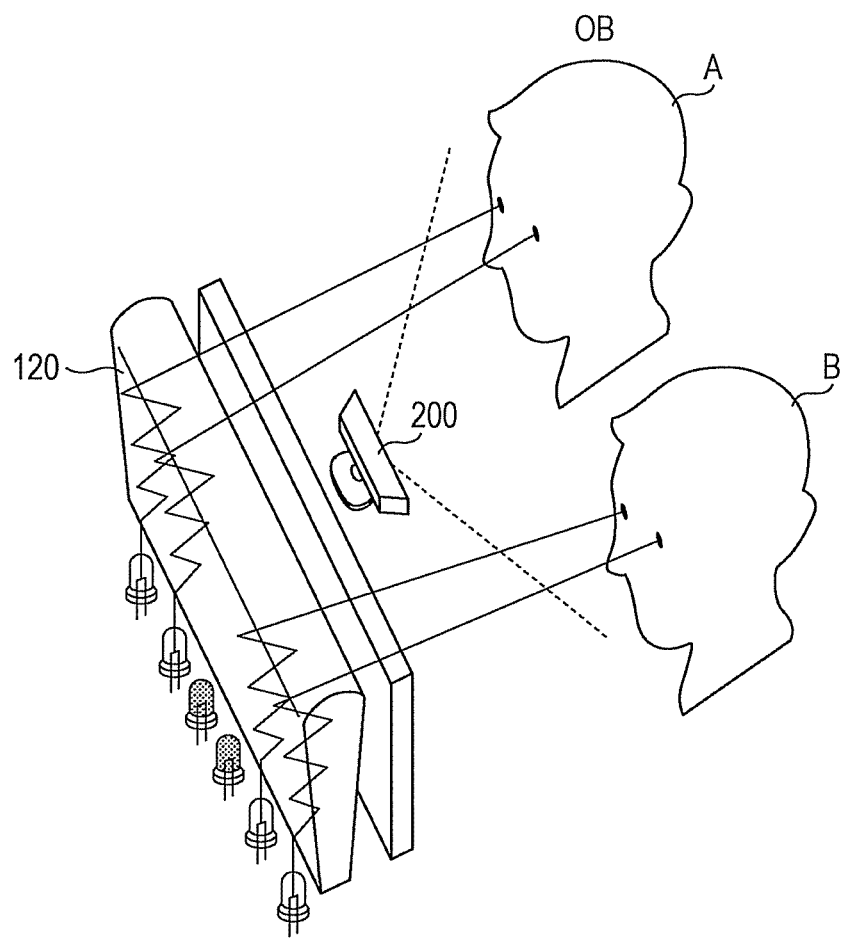
FIG. 9 is a diagram illustrating a 3D image display as an exemplary application of the operator positional tracking in the image display system according to the current invention.

FIG. 9 is a diagram illustrating a 3D image display as an exemplary application of the operator positional tracking in the image display system according to the current invention. For example, the tracking device 200 tracks the position of the head and or the eyes of the operator with respect to a predetermined reference or object such as a display monitor 120 within a predetermined space. As the operator moves his or her dead from a first position A to a second position B, the position of the eyes are also changed with respect to the monitor 120. When the monitor 120 displays a 3D image, if the depth perception is achieved by a difference in the image in the right and left visual field of the operator, the monitor 120 has to update the image in the right and left visual field of the operator as the operator eye position changes. To accomplish this, the tracking device 200 tracks not only the operator whole body movement, but also the eye and or head position in order to properly maintain the depth perception. Although the above image display system is illustrated with respect to the ultrasound imaging and diagnostic systems, the above image display system is not limited to a particular imaging modality according to the current invention.

Still referring to FIG. 9, the above described operator tracking optionally requires additional technology. One exemplary technology is facial recognition to accurately track the eye position of the operator. A facial recognition technology is also optionally combined to keep track of the identity of multiple operators. Theft of expensive imaging probes is a serious problem for medical facilities. The optical, IR camera and microphone could increase chance of the equipment recovery since it can record event when probe(s) are stolen. In order to protect patient and operator privacy, security monitoring should not be turned on all the time but it rather should be triggered by some event, e.g. probe removal etc.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope of the inventions.

Furthermore, the above embodiments are described with respect to examples such as devices, apparatus and methods. Another embodiment to practice the current invention includes computer software such as programs for tracking a predetermined combination of an ultrasound probe, an operator and a patient for the ultrasound system that is loaded into a computer form a recording medium where it is stored.

What is claimed is:

1. A method of tracking an object for ultrasound imaging, comprising the steps of:

emitting electromagnetic radiation having a predetermined wavelength towards a probe and at least one of an operator and a patient from a first predetermined position, the electromagnetic radiation of said emitting step being defined as emitted electromagnetic radiation, the first position being at a distance from a probe;

receiving the electromagnetic radiation reflected from the probe and at least one of an operator and a patient at the first predetermined position, the electromagnetic radiation of said receiving step being defined as reflected electromagnetic radiation;

capturing a first image of the probe and at least one of the operator and the patient at a first point in time at a second predetermined position;

capturing a second image of the probe and at least one of the operator and the patient after the first point in time;

determining a change in distance and angle of the probe and at least one of the operator and the patient in space based upon on the emitted electromagnetic radiation and the reflected electromagnetic radiation, the first image, and the second image; and inputting the change into an ultrasound imaging system.

2. The method of tracking a probe for ultrasound imaging according to claim 1 further comprising a step of displaying certain data according to the change.

3. The method of tracking an object for ultrasound imaging according to claim 2 wherein the data is one of a 2D image, a 3D image and a 4D image that are based upon previously stored data and that corresponds to the change.

4. The method of tracking an object for ultrasound imaging according to claim 2 wherein the data is a 3D volume that is stitched together from a plurality of 3D volumes.

5. The method of tracking an object for ultrasound imaging according to claim 2 wherein the data is a 3D volume that is stitched together from a plurality of 2D images.

6. The method of tracking an object for ultrasound imaging according to claim 2 wherein the data is an image that is based upon imaging data that is acquired by the probe.

7. The method of tracking an object for ultrasound imaging according to claim 2 wherein the data is a 3D volume based upon the change in at least one of distance and angle of the operator.

8. The method of tracking an object for ultrasound imaging according to claim 2 wherein the data is an icon representing the probe based upon the change in at least one of distance and angle of the probe.

9. The method of tracking an object for ultrasound imaging according to claim 8 wherein the data is an image of the patient on which the probe icon is superimposed.

10. The method of tracking an object for ultrasound imaging according to claim 1 wherein the second image is captured at the second predetermined position.

11. The method of tracking an object for ultrasound imaging according to claim 10 wherein the first predetermined position, and the second predetermined position are substantially identical.

12. A system for tracking an object for ultrasound imaging, comprising:
a probe;
a first tracking device configured to
emit electromagnetic radiation having a predetermined wavelength from a first predetermined position being a distance from the probe, and
receive the electromagnetic radiation reflected from the probe and at least one of an operator and a patient at the first predetermined position;
a second tracking device configured to
capture a first image of the probe and at least one of the operator and the patient at a first point in time at a second predetermined position, and
capture a second image of the probe and at least one of the operator and the patient after the first point in time; and
a processing device, connected to the first and second tracking devices, configured to determine a change in distance and angle of the probe based upon on the emitted and reflected electromagnetic radiation received by the first tracking device and the first and second images captured by the second tracking device.

13. The system for tracking an object for ultrasound imaging according to claim 12 wherein the second tracking device and the first tracking device are housed in a common case.

* * * * *